May 30, 1972 H. T. HARTMANN Plant Pat. 3,197

FRUITLESS OLIVE TREE

Filed April 27, 1970 2 Sheets-Sheet 1

INVENTOR
HUDSON T. HARTMANN

Townsend and Townsend ATTORNEYS

FRUITLESS OLIVE TREE
Filed April 27, 1970 2 Sheets-Sheet 2
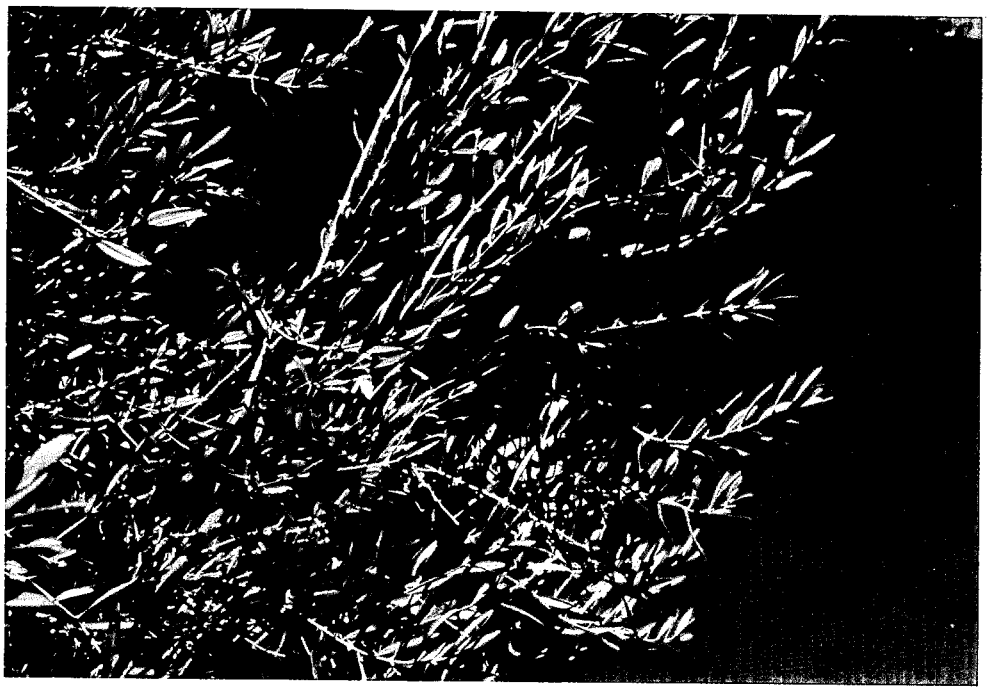
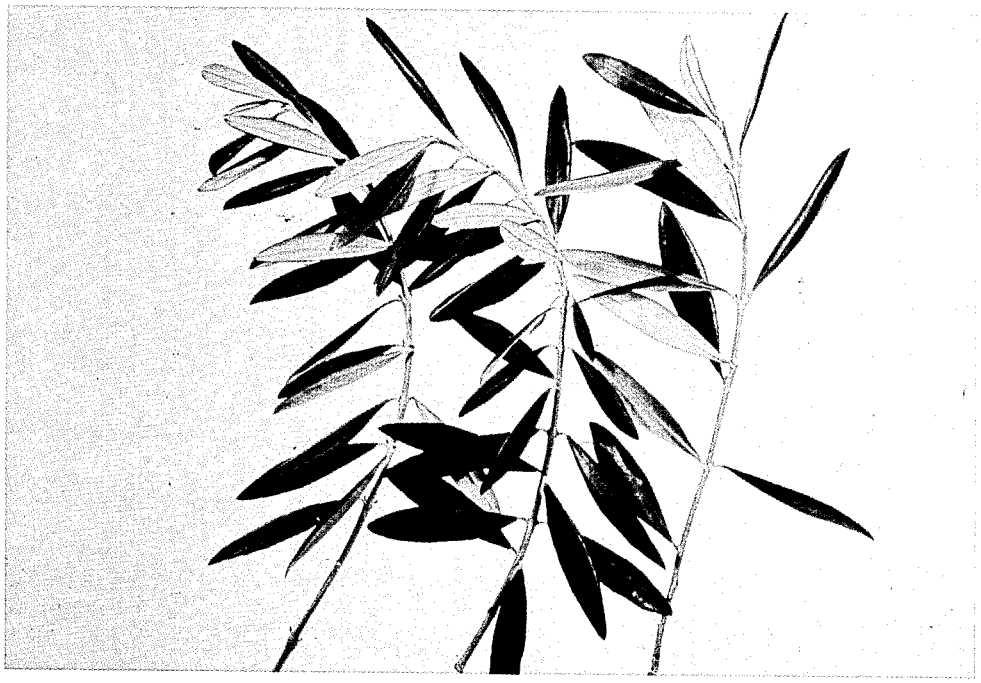
FIG_3
INVENTOR
HUDSON T. HARTMANN
Townsend and Townsend ATTORNEYS United States Patent Office Plant Pat. 3,197
Patented May 30, 1972

3,197
FRUITLESS OLIVE TREE

Hudson T. Hartmann, Davis, Calif., assignor to The Regents of the University of California, Berkeley, Calif.

Filed Apr. 27, 1970, Ser. No. 32,468
Int. Cl. A01h 5/03
U.S. Cl. Plt.—33 1 Claim The present invention relates to a new and distinct variety of olive tree which produces no fruits and which was located in 1961 by me as growing under cultivation near the town of Swan Hill in northern Victoria, Australia. Cuttings were obtained from this tree and shipped to California where they were successfully grafted onto rootstock trees. Such trees have been growing experimentally on The University of California (Davis and Winters) grounds since 1961. From that time these trees propagated by cuttings taken from these original grafts have borne no fruit in any year through the 1969 season. (Trees developed from cuttings taken at the same time in 1961 from known fruiting varieties in Australia, imported into California at the same time, grafted and grown in an identical manner to my new variety, have fruited heavily in California during the 1966, 1967, 1968 and 1969 seasons).

Typical tree characteristics are presented in the accompanying color photographic reproductions:

FIG. 2 shows a typical branch of the tree of FIG. 1; and

FIG. 3 shows typical shoots of the tree of FIG. 1.

Figure 1:
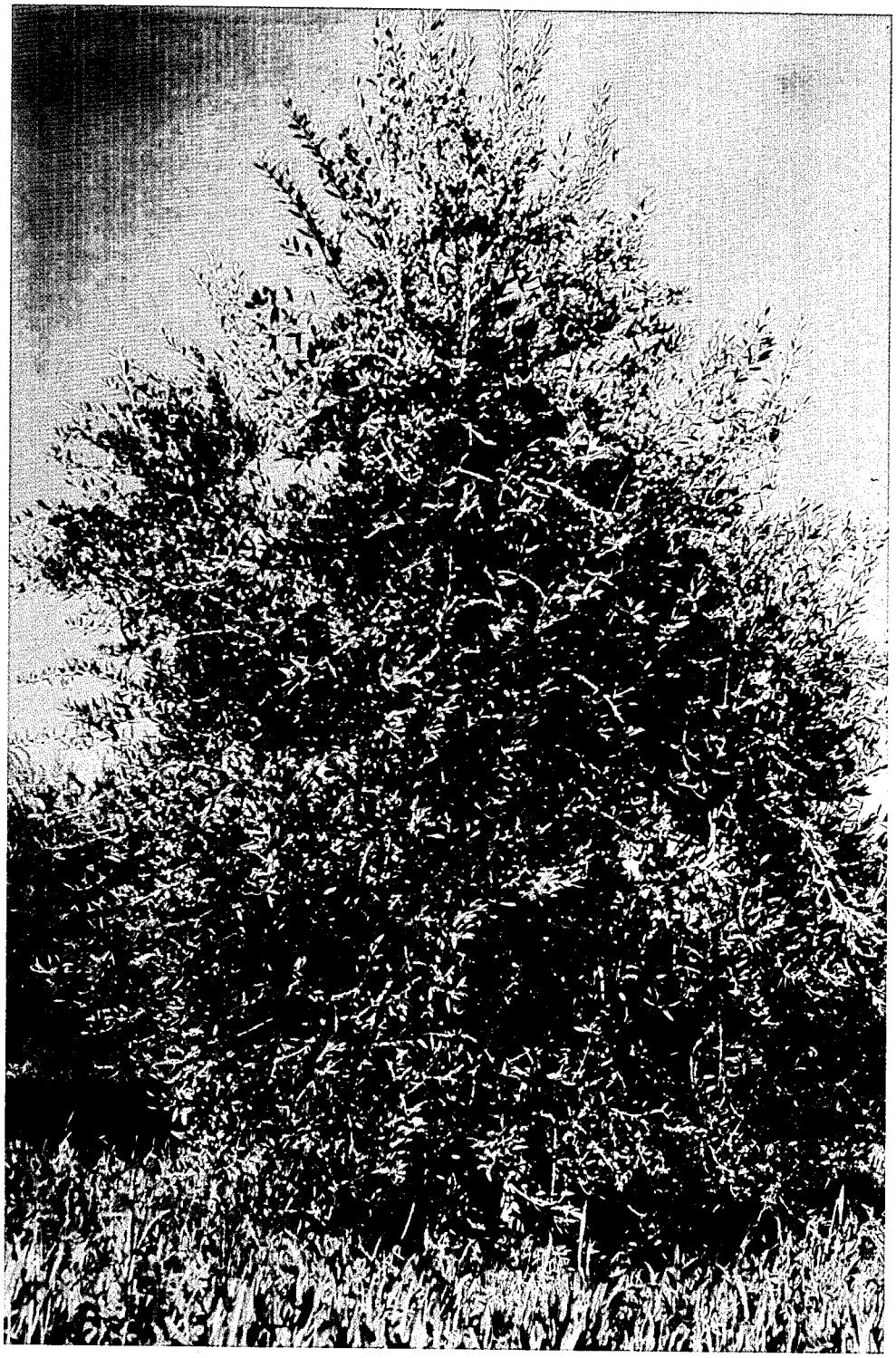
FIG. 1 shows the entire tree as it appears after seven years of growth.

My new variety produces flowers which are almost entirely of the staminate (male) type but which abscise after opening. Flowers of the perfect (male plus female) type are rarely formed but they too abscise without developing into fruits. This is in contrast to commercial fruiting olive varieties which produce an abundance of perfect flowers that develop into fruits and bear commercial olive crops.

The value of my non-fruiting olive tree lies in its use as an ornamental. The evergreen foliage of the olive is very attractive with a dark green color on the upper leaf surface and a silvery gray color on the lower surface. The fruitless characteristic of my new variety makes it particularly desirable as a patio or street tree since this eliminates the troublesome problem of continual fruit dropping throughout the period from late fall to mid-spring.

This new olive variety generally resembles commercial fruiting olive varieties now being grown in California in such characteristics as tree, foliage and trunk appearance. It is similar to existing commercial olive varieties in tree vigor, leaf color, leaf size and shape, size and shape of flower clusters, time of flowering (mid-May at Davis, Calif.), and time of onset of new vegetative growth in the spring (mid-April). It is also similar to commercial fruiting olive varieties in its susceptibility to the fungus disease *Cycloconium oleaginum* (peacock spot) and to the insect pest *Sassitate olea* (black scale).

Asexual reproduction of my new variety, as performed by me by cuttings at Davis, Calif., shows that the distinctive fruitless characteristic comes true to form and is transmitted and established through successive propagations.

I claim:

1. The new and distinct variety of olive tree (*Olea europaea L.*), useful for ornamental purposes, as herein described, characterized particularly as to novelty by its failure to bear fruits.

No references cited.

ROBERT E. BAGWILL, Primary Examiner